(12) United States Patent
Johnson et al.

(10) Patent No.: US 6,264,921 B1
(45) Date of Patent: *Jul. 24, 2001

(54) FLUID DELIVERY SYSTEM AND PROPELLANT MIXTURE THEREFOR

(75) Inventors: Bruce C. Johnson, Loretto; Dennis Norgon, Andover; Paul Kratoska, Brooklyn Park, all of MN (US)

(73) Assignee: Medtronic, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/641,187

(22) Filed: Apr. 30, 1996

(51) Int. Cl.[7] ........................................... A61K 9/12
(52) U.S. Cl. ................................. 424/45; 424/46
(58) Field of Search ......................... 424/45, 46

(56) References Cited

U.S. PATENT DOCUMENTS

| | | | |
|---|---|---|---|
| 4,174,295 | * | 11/1979 | Bargigia et al. . |
| 4,505,710 | | 3/1985 | Collins . |
| 5,336,816 | | 8/1994 | Achord et al. . |
| 5,800,729 | * | 9/1998 | Wilson et al. . |

FOREIGN PATENT DOCUMENTS 0 275 695    7/1988  (EP) .
95/01775     1/1995  (WO) .

OTHER PUBLICATIONS

Brochure issued by DuPont entitled "Alternatives to Chlorofluorocarbons," Jan. 1992.
Chart issued by 3M entitled "3M Performance Fluids—Comparison Guide," Feb. 1994.
Brochure issued by 3M entitled "1993 Fluorinert™ Liquids—Typical Properties Chart," Jan. 1993.
Brochure issued by 3M entitled "Fluorinert™ Liquids—Unique Perfluorinated Liquids for Thermal Management, Vapor Phase Reflow Soldering, Electronic Testing, Alternative Fluids for CFCs," Feb. 1991.
Brochure issued by 3M entitled "Liquid Burn–In Testing with Fluorinert Liquids," Apr. 1993.
Brochure issued by 3M entitled "Fluorinert™ Liquid Heat Sink Technical Description and Application Data," Dec. 1990.
Product Manual issued by 3M entitled "Fluorinert™ Liquids," (undated).

* cited by examiner

*Primary Examiner*—Raj Bawa
(74) *Attorney, Agent, or Firm*—Eric R. Waldkoetter; Curtis D. Kinghorn; Tom G. Berry

(57) ABSTRACT

A fluid delivery system and a propellant therefor. The propellant comprises a mixture of a plurality of substances, the precise by-weight or by-molar combination of which is used to set the propellant pressure within a desirable pressure range. At least one of the plurality of propellant substances is a relatively higher vapor pressure fluid; and at least one of the plurality of propellant substances is a relatively lower vapor pressure fluid.

12 Claims, 1 Drawing Sheet

FLUID DELIVERY SYSTEM AND PROPELLANT MIXTURE THEREFOR

FIELD OF THE INVENTION

The present invention relates generally to "gas driven" implantable drug pumps and, more specifically, to propellants for such pumps that provide a substantially constant pressure to the drug fluid reservoir of the pump so that the drug fluid can be delivered at a substantially constant rate.

BACKGROUND OF THE INVENTION

It is desirable that drug therapy or, more specifically, the drug fluid being provided from the drug fluid reservoir of an implantable drug pump be provided at a substantially constant rate. Conventional practice achieves the substantially constant rate by use of only a single substance or fluid that acts as a pressure-providing means. The substance typically used to drive such a "gas driven" pump is a fluid that is in phase change between a liquid state and a gas state when, i.e., in equilibrium between phases at around 37 degrees (Celsius), which is the usual temperature of the human body.

Three known examples of fluids that are each used as the single propellant for gas-driven implantable pumps are (1) R-11, a propellant that is used, for example, in the commercially available Infusaid drug pump; (2) R-114, a propellant that is used in commercially available TricuMed drug pumps; and (3) n-butane, a well known and commercially available substance also used in TricuMed implantable drug pumps.

The R-11 propellant supplies approximately 8.5 p.s.i.g. to the drug reservoir of a known drug pump, the Infusaid model, at 37 degrees (Celsius). Two known TricuMed drug pumps use R-114, the 35.1 and 20.1 models. The R-114 propellant supplies about 31 p.s.i.g. at 37 degrees (Celsius) to the reservoirs of those drug pumps. The n-butane propellant, used in the drug reservoirs of TricuMed's version 20.2 and 35.2 drug pumps, provides a reservoir pressure of 36 p.s.i.g. at around 37 degrees (Celsius).

There are, however, many disadvantages that result with the use of either of the above-mentioned single-substance propellants. The disadvantages relate to the preservation of earth's environment, fundamental operability of drug pumps under changing conditions, safety during manufacture, and ease of use during clinical preparations.

Specifically, the known, singly-used propellants R-11 and R-114 are both chloro-fluoro-carbons, also commonly referred to as CFCs. These substances are thought to deplete the protective ozone layer of the atmosphere of the earth. As a result, the use of CFCs is being limited or eliminated throughout the earth. Meanwhile, the diminishing production of such fluids has made them increasingly expensive to obtain and, therefore, to use.

Additionally, use of a propellant such as R-11, which has low pressure as a characteristic property, raises functionality issues. Specifically, an 8.5 p.s.i.g. propellant reservoir pressure, such as is provided using R-11, is so low a pressure that when changes of temperature, altitude and/or drug reservoir volume occur, the propellant reservoir pressure varies substantially, adversely impacting the accuracy of drug delivery.

Use of the propellant R-114, which as stated above is used for a 31 p.s.i.g. pump reservoir pressure, is disadvantageous because of clinical use problems. Specifically, the characteristic pressure of such a propellant is so high that a clinician has extreme difficulty (re)filling the drug reservoir of the implantable drug pump with drug fluid.

Another clinical use problem arises with the use of n-butane as the propellant. This propellant is not a CFC, but it is also a high pressure fluid. The 36 p.s.i.g. reservoir pressure associated with n-butane is even worse than R-114 from the standpoint that the clinician has extreme difficulty (re)filling the pump. Moreover, n-butane is flammable. Thus, since propellant fluid is welded into the drug pump (behind or below the pump's bellows reservoir), use of a flammable substance, such as n-butane, necessarily creates a significant risk of hazard.

In sum, conventional single-substance propellants have forced designers to confront the environmental hazards of CFCs (and also toxicity), and to choose between using either (a) a relatively easier to (re)fill, lower-pressure propellant which offers lower flow rate accuracy, or (b) a relatively much more difficult to (re)fill higher pressure propellant, which offers higher flow rate accuracy.

SUMMARY OF THE INVENTION

As explained in more detail below, the present invention overcomes the abovenoted and other shortcomings of conventional propellants for gas-driven, fixed-rate, implantable drug pumps.

The present invention comprises a propellant mixture for gas-driven implanted drug pumps having an intermediate pressure (for example, 20 p.s.i.g.) that allows for high accuracy and relatively easy (re)filling. The present invention does not involve the use of CFCs or flammable or toxic fluids and, in fact, under its teachings, any desired pressure within a substantial pressure range can be achieved (for example, 5 to 40 p.s.i.g.).

The present invention allows for a propellant that comprises a mixture of a plurality of substances, the precise by-weight or by-molar combination of which is used to set the propellant pressure within a desirable pressure range. The present invention further comprises a method for filling the pump reservoir with the propellant mixture to ensure that the desired and selected pressure setting for any pump is accurately achieved.

At least one of the plurality of propellant substances is a relatively higher vapor pressure fluid; and at least one of the plurality of propellant substances is a relatively lower vapor pressure fluid. These fluids are mixed to yield the desired reservoir vapor pressure at body temperature, i.e., at around 37 degrees (Celsius). The mixing process of the present invention enables the constituent substances of the plurality to be mixed without permitting the higher vapor pressure substance (which has a relatively lower boiling point) to boil off, altering the mixture and its characteristic pressure away from the desired pressure. Specifically, according to the teaching of the present invention, one step of the mixing and filling process involves keeping the temperature of the drug pump, of the tubing connecting the drug pump to the propellant supplies, and of the supplies of the plurality of propellant substances at a sufficiently cool temperature throughout propellant filling and propellant chamber sealing to ensure that each of the plurality of propellant fluids is maintained at a temperature below the lower boiling point.

The foregoing features of the present invention have been broadly outlined in order that the detailed description that follows may be understood and so that contributions which the invention provides to the art may be better appreciated. The invention is described in greater detail below, with additional features being set forth with reference to the figures provided and included within the subject matter of the claims appended hereto.

DETAILED DESCRIPTION OF THE INVENTION

Figure 1:
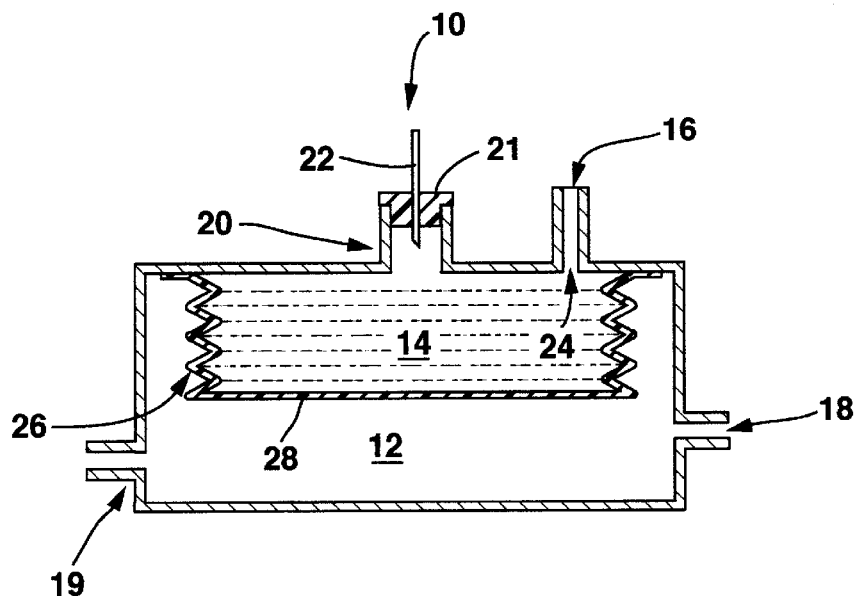
FIG. 1 is an illustration of a gas-driven, implantable drug pump of the kind in which the propellant mixture of the present invention may be used.

A gas-driven, implantable drug pump 10 of the kind in which the propellant mixture of the present invention may be used is depicted in FIG. 1. As shown, drug pump 10 includes a propellant chamber 12, a fluid or drug fluid ("bellows") reservoir 14, and a fluid or drug fluid delivery channel or lumen 16: Drug pump 10 further includes a propellant introduction inlet 18 (sealed after filling) an air evacuation aperture 19 (also sealed after filling), and a fluid injection port 20 with a septum 21. Drug pump 10 operates with one or more introducer needles 22 that are used to introduce fluid beyond injection port 20 and into reservoir 14.

The propellant mixture of the present invention is stored in propellant chamber 12 to "power" delivery of drug fluid, which is stored in drug fluid reservoir 14 of drug pump 10. The propellant mixture of the present invention, as described in greater detail below, comprises a plurality of propellant substances in phase change between the liquid and vapor states at or around normal body temperature, i.e., about 37 degrees (Celsius), i.e., in phase equilibrium. Thus, when drug pump 10 is implanted, the propellant mixture is retained in a vapor pressurized condition capable of providing a sustained force to drive continuous drug delivery.

Structurally, as shown in FIG. 1, drug fluid reservoir 14 may be encompassed within propellant chamber 12, but with reservoir 14 and chamber 12 each being sealed and not in fluid communication with each other. Propellant chamber 12 may be situated around and below fluid reservoir 14, with the top side of fluid reservoir 14 being a rigid top surface having located therein injection port 20 and an opening 24 that creates a fluid passageway between fluid reservoir 14 and delivery channel 16. A flexible accordion- or bellows-type wall 26 defines the circumferential boundary between propellant chamber 12 and drug fluid reservoir 14. Another, relatively non-elastic wall 28 partitions fluid reservoir 14 and propellant chamber 12 on the bottom side of fluid reservoir 14. In this embodiment, the vapor pressure of the propellant mixture in propellant chamber 12 imposes force on fluid reservoir 14, and particularly on bottom wall 28 pushing it upward and against the drug fluid stored in drug fluid reservoir 14. Drug fluid, under pressure in drug fluid reservoir 14, advances toward opening 24 and through delivery channel 16, which, as stated above, is in fluid communication with drug fluid reservoir 14 through opening 24. At a proximal portion of delivery channel 16 (not shown) adjacent to the tissue sought to be treated, drug fluid is ejected from delivery channel 16 and infused into the tissue to be treated.

As will be appreciated by those of ordinary skill in this area, the fact that the propellant in propellant chamber 12 is in phase change, i.e., in equilibrium between liquid and vapor phases is critical to the operation of a "gas-driven" pump such as drug pump 10. Because liquid propellant changes state to gas as the store of drug fluid in reservoir 14 is reduced, the fluid system in propellant chamber 12, comprising the propellant mixture of the present invention, can provide a consistent level of pressure without requiring an increase in temperature above that of the human body.

As discussed above, conventional implantable drug pumps use a single substance in the propellant chamber. However, the present invention provides a propellant mixture in propellant chamber 12. Moreover, unlike conventional propellants, the propellant mixture of the present invention comprises materials that are non-flammable, that are not toxic and that are not CFCs. The constituent materials are blended to deliver a consistent and desirable operating pressure; and the precise selection of the constituent substances and their relative proportions in the mixture determines the particular pressure that is provided to the drug fluid by the propellant mixture. Because the pressure of the propellant mixture can be adjusted within a range, the pressure can be set to be both low enough to make it relatively easier for a clinician using, for example, one or two successive, appropriately-sized needles 22 to (re)fill drug fluid reservoir 14, and yet high enough to provide a consistent force to drug fluid reservoir 14 even over a wide range of operating conditions, i.e., varying temperature, altitude, and drug fluid reservoir volume.

Specifically, the propellant of the present invention comprises a mixture of a plurality of substances, combined in a by-weight or by-molar manner to achieve a desired characteristic pressure. The pressure of the propellant mixture may be set to, for example, between 5 and 40 p.s.i.g. and, preferably for certain uses, may be set at an intermediate level, such as 20.0 p.s.i.g., to achieve more noticeably the above-described dual advantages of accuracy and ease of (re)filling.

The plurality of substances of the propellant mixture of the present invention includes at least one substance having a relatively higher vapor pressure. This substance is chosen to be miscible with and impart to the propellant mixture the higher accuracy operating feature. One preferred substance, usable as the relatively higher vapor pressure constituent, is refrigerant or solvent "142b," a solvent commercially available from Allied Signal, Inc. of Morristown, N.J. as one of its "Genensolv 2000 Series Solvents." Like traditionally used single solvents, solvent 142b's molecular structure includes two carbon atoms. Its other atoms, however, are chlorine, fluorine, and hydrogen atoms. Specifically, the exemplary solvent 142b includes one carbon atom with three hydrogen atoms bonded thereto, and another carbon atom bonded to one chlorine atom and two fluorine atoms (1,chloro,1,1,difluoroethane, which is symbolized as $CH_3CClF_2$). Thus, solvent 142b is not a CFC, but it is instead an HCFC, which has a much shorter lifetime in the atmosphere in comparison with CFCs and, therefore, 142b has a greatly reduced impact on stratospheric ozone depletion. This solvent, which is given by way of example only, also has low toxicity and is resistant to flammability when subjected to spark tests.

The characteristic vapor pressure of this particular substance, solvent 142b, is 70.0 p.s.i.g. (at body temperature) and its boiling point is 14.40 degrees (Fahrenheit). It has a molar weight of 100.47.

Specifically, the presence of a higher vapor pressure substance, e.g., 142b, imparts to the solvent mixture a higher vapor pressure characteristic at body temperature in proportion to the ratio of the molar weight of this substance in the propellant mixture introduced into propellant chamber 12 to the molecular weight of the lower pressure substance in the propellant mixture (i.e., the mole fraction). Thus, in view of the relatively much higher pressure, 70.0 p.s.i.g., of 142b in comparison with a desired pressure such as 20.0 p.s.i.g., the proportion of 142b in the propellant mixture will likely be small (less than 0.50 mole fraction) in comparison with that of a lower vapor pressure fluid. As indicated above, the boiling point of a higher vapor pressure substance is relatively low, and in the case of 142b only 14.40 degrees (Fahrenheit), which is substantially below body or typical room temperature. Accordingly, special handling procedures, as described in greater detail below, are necessary when preparing this substance for use in drug pump 10.

The plurality of substances of the propellant mixture of the present invention also includes at least one substance having a relatively lower vapor pressure. This substance is chosen to be miscible with and to impart to the propellant mixture the greater ease of (re)filling feature. One preferred substance usable as the relatively lower pressure constituent is solvent "141b," a solvent that is also commercially available from Allied Signal, Inc. of Morristown, N.J. as one of it Genesolv 2000 Series Solvents. Like single solvents that are traditionally used as drug pump propellants, solvent 141b has a molecular structure that includes two carbon atoms. However, 141b's structure like that of 142b includes chlorine, fluorine, and hydrogen atoms. Specifically, solvent 141b, which is merely intended to be illustrative of the type of relatively lower pressure solvent that may be used, includes one carbon atom with three hydrogen atoms bonded thereto, and another carbon atom bonded to one fluorine atom and to two chlorine atoms (1,1,dichloro,1,fluoroethane, which is symbolized as $CH_3CCl_2F$). Thus solvent 141b is also not a CFC, but also an HCFC, which brings with it the reduced impact on ozone depletion. Solvent 141b also has low toxicity, and is non-flammable.

With respect to physical properties, solvent 141b has a characteristic vapor pressure of 17.50 p.s.i.g. (at body temperature), and a boiling point of 89.60 degrees (Fahrenheit). Its molar weight is 116.95.

The presence of a lower vapor pressure substance, e.g., 141b, imparts to the solvent mixture a lower pressure characteristic at body temperature in proportion to the ratio of the molar weights of the substances in the propellant mixture (i.e., the mole fractions) that are introduced into propellant chamber 12. Specifically, to the extent the characteristic vapor pressure of the lower pressure substance is only relatively slightly below a desired characteristic pressure for the propellant mixture, e.g., 20.0 p.s.i.g., the proportion of the lower vapor pressure substance will be large (possibly much more than 0.50 mole fraction) in comparison with that of a higher vapor pressure a fluid.

The propellant mixture of the present invention, comprising at least a higher pressure and a lower pressure substance as described above, is of sufficiently high pressure to provide constancy of pressure under changing conditions. For example, where the above described solvents 141b and 142b are combined to achieve a mixture having a characteristic pressure of 20.0 p.s.i.g., temperature variations within the body, altitude changes and variations in the volume of fluid in fluid reservoir 14 will have minimal impact on the pressure provided by the propellant mixture. The mixture easily provides relatively constant pressure over a temperature range from 35 to 39 degrees (Celsius). Similarly, altitude changes from, for example, 0 to 5000 feet above sea level, and fluid reservoir volume changes from, for example, 21.0 ccs. (full) to 2.0 ccs. (effectively empty) do not substantially alter the pressure provided by the propellant mixture. Hence, the flow rate of drug fluid into and through delivery channel 16 varies only a modest amount, under changing conditions.

The characteristic pressure of the propellant mixture of the present invention also is sufficiently low to allow a clinician (re)filling drug fluid reservoir 14 to do so using a modest and comfortable amount of force. As indicated above, fluid reservoir 14 may have, for example, a capacity of essentially 20.0 ccs. In this case, the clinician can choose to fill fluid reservoir 14 using only a single 20.0 cc. needle. Alternatively, to reduce the force required, the clinician may fill reservoir 14 using two 10.0 cc. needles. Since the propellant mixture of the present invention does not require the application of an uncomfortable force with a needle 22 placed into septum 21 of injection part 20, it is possible for a clinician to over-pressurize fluid reservoir 14 by introducing an excessive quantity of fluid. Accordingly, over-pressure protection may be introduced for drug pumps expected to be used in situations where over-pressurization by a clinician is likely.

Again, it should be understood that the above-referred to substances, 141b and 142b, are given only by way of example, and that the present invention may be practiced to achieve the foregoing advantages using other substances. For example, an alternative propellant mixture may be arrived at using R-134a and Ventrel 245. The refrigerant or solvent R-134a is a relatively higher pressure substance available from Allied Signal, the DuPont Company, or other chemical manufacturers. This substance is often used as a refrigerant in cooling systems and its properties are generally known by those of ordinary skill in the art. Ventrel 245, a relatively lower pressure fluid, is also known to those of ordinary skill. It is commercially available from the DuPont Company. Yet another propellant mixture comprises a blend of propane and butane as the higher and lower pressure fluids, respectively. This latter mixture does, however, reintroduce flammability concerns.

As stated above, use of the unique propellant mixture of the present invention creates a situation in which a specialized procedure for filling propellant chamber 12 is useful. Specifically, filling propellant chamber 12 with the propellant mixture of the present invention without having the higher vapor pressure substance (e.g., solvent 142b) boil off, thus altering the mixture, requires the creation and maintenance of controlled conditions while the propellant chamber 12 is filled with the constituents of the propellant mixture. The controlled conditions ensure that, when filling is complete and propellant chamber 12 is sealed, the mixture residing in propellant chamber 12 comprises the full amount of the constituent substances sought to be transferred to propellant chamber 12.

Figure 2:
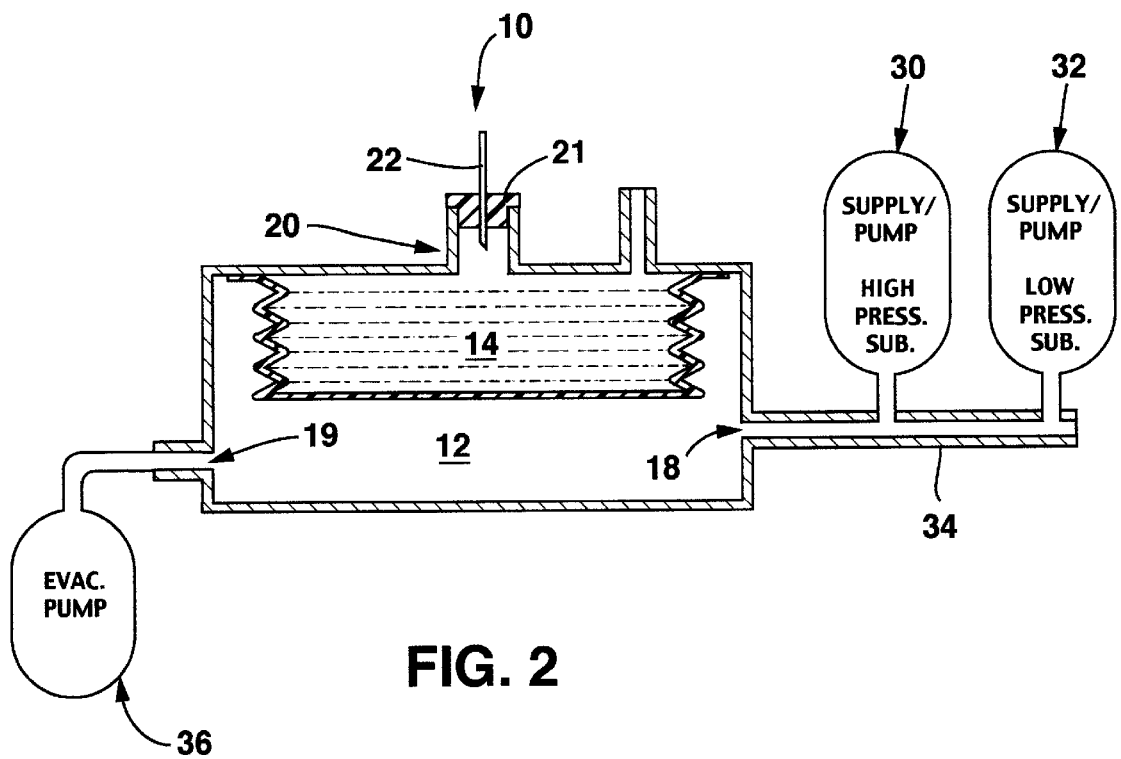
FIG. 2 is an illustration of the procedure by which the propellant chamber of a drug pump having the propellant mixture of the present invention is filled with that propellant mixture.

According to the present invention, the filling of propellant chamber 12 requires obtaining supplies of each of the substances of the propellant mixture, including a supply (and pump) 30 of at least one relatively higher pressure substance and a supply (and pump) 32 of at least one relatively lower pressure substance that are to be in phase change state in chamber 12 when at or about body temperature (see FIG. 2). The boiling points of the substances of the mixture having the lower and higher boiling points must be determined. The supplies 30 and 32 of the substances with the lower and higher boiling points are each maintained at a temperature below the lower boiling point of the relatively higher pressure substance. The supplies 30 and 32 of these substances will then be connected by a fluid passageway 34 to introduction inlet 18 of chamber 12, which will be maintained unsealed until the desired amounts of the propellant mixture substances from supplies 30 and 32 have been transferred to chamber 12. (Of course, separate passageways may be used without departing from the general teaching of the present invention). Chamber 12 also will be maintained at a temperature below that of the lower boiling point by refrigeration means. Pre-determined amounts of each substance that together achieve a by-molar mixture with the desired characteristic pressure for the propellant mixture are then released from the supplies 30 and 32 to chamber 12. Air is eliminated from chamber 12 by an evacuation pump 36 drawn on the pre-chilled space of chamber 12 in order to allow the substances of the propellant mixture to comprise the only ingredients on chamber 12. After the desired amounts of each of the substances of the propellant mixture are transferred to chamber 12 from supplies 30 and 32, and all air evacuated, injection inlet 18 and evacuation aperture 19 are sealed to maintain the propellant mixture in the air tight environment of chamber 12.

As an alternative technique, the advantages of which will be easily understood by those of ordinary skill, evacuation aperture 19 may be eliminated altogether. A single inlet 18 may be used both to evacuate air and introduce the ingredients of the propellant mixture. This may be done by providing apparatus such as a three-way valve or valve control system with fluid passageway 34 and by placing evacuation pump 36 in fluid communication with passageway 34. This arrangement would involve evacuating air from chamber 12 through inlet 18 using pump 36, and then closing a valve connecting passageway 34 to pump 36. Thereafter, valves to supplies 30 and 32 can be opened to allow filling of chamber 12 through passageway 34 and inlet 18 with the constituent substances from supplies 30 and 32.

In yet another preferred embodiment, the substances in supplies 30 and 32 may be pre-mixed off-line and then provided to a pre-mixed pump/supply for valving onto passageway 36 and through inlet 18 into chamber 12.

It should be noted that the above-described propellant mixture and method for filling the propellant chamber with that mixture affords substantial flexibility for a drug pump design. Adjustments in the proportions of the mixture ingredients allow a designer to achieve any particular characteristic pressure to obtain a particular balance between accuracy and ease of clinical use appropriate for different drugs pumps and situations. Gas-driven drug pump or other device which works on the same principles will no longer need to have only one of the single characteristic pressures available using a limited number of single-substance propellants.

Although the preferred embodiment of this invention has been described in some detail, it should be appreciated that a variety of embodiments will be readily available to persons utilizing the invention for a specific end use. The description of the apparatus and method of this invention is not intended to be limiting on this invention, but is merely illustrative of the preferred embodiment of this invention. Other apparatus and methods which incorporate modifications or changes to that which has been described herein are equally included within this application. Additional objects, features and advantages of the present invention will become apparent by referring to the above description of the invention in connection with the accompanying drawings.

What is claimed is:

1. A propellant mixture for a gas-driven fluid delivery system, comprising:
   a first fluid having a first vapor pressure, the first being 1,chloro,1,1-difluoroethane (CH3CClF2); and
   a second fluid having a second vapor pressure which is less than the first vapor pressure, the second fluid being 1,1-dichloro, 1-fluoroethane ($CH_3CCl_2F$);
   the first and second fluids being combined to produce a propellant mixture which changes phase from liquid to gas at about 37 degrees Celsius to produce a characteristic vapor pressure of the propellant mixture of between 5 and 40 p.s.i.g. for operating a gas-driven fluid delivery system.

2. The propellant mixture of claim 1, wherein the characteristic vapor pressure of the propellant mixture is approximately 20 p.s.i.g.

3. The propellant mixture of claim 1, wherein the vapor pressure of the first fluid is above 40 p.s.i.g. and the vapor pressure of the second fluid is below 20 p.s.i.g.

4. A propellant mixture for a gas-driven fluid delivery system, comprising:
   a first fluid having a first vapor pressure, the first fluid being 1,1,1,2-tetrafluoroethane (CH2FCF3); and
   a second fluid having a second vapor pressure which is less than the first vapor pressure, the second fluid being perfluoro-dimethylcyclobutane (C6F12);
   the first and second fluids being combined to produce a propellant mixture which changes phase from liquid to gas at about 37 degrees Celsius to produce a characteristic vapor pressure of the propellant mixture of between 5 and 40 p.s.i.g. for operating a gas-driven fluid delivery system.

5. A gas-driven fluid delivery system having a propellant mixture for driving delivery of the fluid, comprising:
   a fluid reservoir for receiving a fluid to be delivered;
   a propellant chamber adjacent to the fluid reservoir; and
   a first fluid and a second fluid disposed within the propellant chamber as a propellant mixture, the first fluid being 1, chloro,1,1-difluoroethane (CH3CClF2) and having a first vapor pressure, the second fluid being 1,1-dichloro,1-fluoroethane ($CH_3CCl_2F$) and having a second vapor pressure which is less than the first vapor pressure, the first and second fluids being combined such that the propellant mixture changes phase from liquid to gas at about 37 degrees Celsius to produce a characteristic vapor pressure of the propellant mixture of between 5 and 40 p.s.i.g. for driving the fluid to be delivered from the fluid reservoir.

6. The gas-driven fluid delivery system of claim 5, wherein the characteristic vapor pressure of the propellant mixture is approximately 20 p.s.i.g.

7. The gas-driven fluid delivery system of claim 5, wherein the characteristic vapor pressure of the first fluid is above 40 p.s.i.g. and the characteristic vapor pressure of the second fluid is below 20 p.s.i.g.

8. A gas-driven fluid delivery system having a propellant mixture for driving delivery of the fluid, comprising:
   a fluid reservoir for receiving a fluid to be delivered;
   a propellant chamber adjacent to the fluid reservoir; and
   a first fluid and a second fluid disposed within the propellant chamber as a propellant mixture, the first fluid being 1,1,1,2-tetrafluoroethane (CH2FCF3) and having a first vapor pressure, the second fluid being perfluoro-dimethylcyclobutane (C6F12) and having a second vapor pressure which is less than the first vapor pressure, the firsst and second fluids being combined such that the propellant mixture changes phase from liquid to gas at about 37 degrees Celsius to produce a characteristic vapor pressure of the propellant mixture of between 5 and 40 p.s.i.g. for driving the fluid to be delivered from the fluid reservoir.

9. The propellant mixture of claim 1, wherein the first and second fluids are combined in a by-weight manner.

10. The propellant mixture of claim 1, wherein the first and second fluids are combined in a by-molar manner.

11. The gas-driven fluid delivery system of claim 5, wherein the first and second fluids are combined in a by-weight manner.

12. The gas-driven fluid delivery system of claim 5, wherein the first and second fluids are combined in a by-polar manner.

* * * * *